(12) United States Patent
Funaya et al.

(10) Patent No.: US 9,339,257 B2
(45) Date of Patent: May 17, 2016

(54) MEASURING APPARATUS AND METHOD THEREOF

(71) Applicant: GE Medical Systems Global Technology Company, LLC, Waukesha, WI (US)

(72) Inventors: Seiji Funaya, Toyko (JP); Koji Miyama, Tokyo (JP); Yasuyo Saito, Tokyo (JP); Masafumi Ogasawara, Tokyo (JP)

(73) Assignee: GENERAL ELECTRIC COMPANY, Schenectady, NY (US)

(*) Notice: Subject to any disclaimer, the term of this patent is extended or adjusted under 35 U.S.C. 154(b) by 34 days.

(21) Appl. No.: 14/087,899

(22) Filed: Nov. 22, 2013

(65) Prior Publication Data

US 2014/0148695 A1    May 29, 2014

(30) Foreign Application Priority Data

Nov. 29, 2012   (JP) .................................. 2012-260774

(51) Int. Cl.
| | | |
|---|---|---|
| A61B 8/08 | (2006.01) | |
| G06T 7/20 | (2006.01) | |
| A61B 5/026 | (2006.01) | |

(52) U.S. Cl.
CPC ................ *A61B 8/5215* (2013.01); *A61B 5/026* (2013.01); *A61B 8/0891* (2013.01); *G06T 7/2033* (2013.01); *A61B 8/485* (2013.01); *G06T 2207/10132* (2013.01)

(58) Field of Classification Search
None
See application file for complete search history.

(56) References Cited

U.S. PATENT DOCUMENTS

| | | | |
|---|---|---|---|
| 7,959,572 B2 | 6/2011 | Ishihara | |
| 8,475,382 B2 | 7/2013 | Mihama et al. | |
| 2008/0262354 A1 | 10/2008 | Yoshida et al. | |
| 2010/0069755 A1 | 3/2010 | Nishimura et al. | |
| 2011/0245673 A1 | 10/2011 | Kamiyama | |
| 2012/0108971 A1* | 5/2012 | Miyama ................... | A61B 8/06 600/443 |
| 2012/0108972 A1* | 5/2012 | Miyama ................... | A61B 8/08 600/443 |
| 2012/0179042 A1 | 7/2012 | Fukumoto et al. | |

FOREIGN PATENT DOCUMENTS

| | | |
|---|---|---|
| JP | 2002238903 | 8/2002 |
| JP | 2007-275457 | 10/2007 |

(Continued)

OTHER PUBLICATIONS

Evans, David H. et al., Ultrasonic Colour Doppler Imaging Interface Focus 2011; pp. 490-502; DOI: 10.1098/rsfs.2011.0017; published Jun. 27, 2011; accessed on Jun. 7, 2015 at <http://rsfs.royalsocietypublishing.org/content/1/4/490>.

*Primary Examiner* — Utpal Shah
*Assistant Examiner* — Kate R Duffy

(57) ABSTRACT

A measuring apparatus is provided. The measuring apparatus includes a measurement reference part setting unit configured to set-measurement reference parts to each of a plurality of sequential ultrasound images of a subject, a tracking unit configured to perform tracking of a plurality of regions in the ultrasound images, a first motion information calculating unit configured to calculate first motion information of the regions, based on the tracking performed by the tracking unit, and a second motion information calculating unit configured to calculate second motion information of the measurement reference parts, based on the first motion information, wherein the plurality of regions move with the measurement reference parts and include parts capable of capturing moving factors that are not able to be captured by tracking the measurement reference parts between a first ultrasound image and a second ultrasound image using the tracking unit.

11 Claims, 12 Drawing Sheets

(56) References Cited

FOREIGN PATENT DOCUMENTS

| JP | 2008173387 | 7/2008 |
| JP | 2009-045251 | 3/2009 |
| JP | 2010110373 | 5/2010 |
| JP | 2012090819 | 5/2012 |
| JP | 2012090820 | 5/2012 |
| JP | 2012090821 | 5/2012 |
| JP | 2012183261 | 9/2012 |
| WO | 2011099103 | 8/2011 |

* cited by examiner

MEASURING APPARATUS AND METHOD THEREOF

CROSS REFERENCE TO RELATED APPLICATIONS

This application claims the benefit of Japanese Patent Application No. 2012-260774 filed Nov. 29, 2012, which is hereby incorporated by reference in its entirety.

BACKGROUND OF THE INVENTION

The present invention relates to a measuring apparatus that tracks movements of parts to which regions of interest set to an ultrasound image are set, and a control program thereof.

The early sensing of a sign of arteriosclerosis is effective in preventing a circulatory system disease such as brain infarction, myocardial infraction or the like. Observing a blood vessel using an ultrasonic diagnostic apparatus has been conducted as a check on the arteriosclerosis. There has been described in, for example, Japanese Unexamined Patent Publication No. 2002-238903 and Japanese Unexamined Patent Publication No. 2012-90820 that to perform a diagnosis of the arteriosclerosis, regions are set to a vascular wall of an ultrasound image and the movement of each part to which the regions has been set is tracked.

Incidentally, the tracking of the movement of each part to which the regions have been set, is done based on a brightness distribution of each ultrasound image. Thus, when a similar brightness distribution is taken in a moving direction, accurate tracking becomes difficult. Described specifically, moving factors of a vascular wall include various factors such as a movement based on the operation of urging an ultrasonic probe being brought into contact with a body surface of a subject, a movement based on the operation of the subject, a movement by respiration, a movement of vasoconstriction due to pulsation, a movement in a vascular major-axis direction due to an inertia force with the movement of blood within a blood vessel, etc.

Even when of these, the movement of the blood vessel in its major-axis direction (horizontal direction) due to the inertia force with the movement of blood is taken in, for example, a major-axis direction cross-section image of a blood vessel extending in a horizontal direction, a vascular wall takes a similar brightness distribution in the horizontal direction, and regions targeted for tracking are not so large that accurate tracking becomes difficult. With the foregoing in view, there has been a demand for a measuring apparatus capable of obtaining accurate motion information about measurement reference parts each defined as a reference for the execution of measurements

BRIEF DESCRIPTION OF THE INVENTION

In a first aspect, a measuring apparatus is provided. The measuring apparatus is equipped with a measurement reference part setting unit which sets measurement reference parts to each ultrasound image of a subject, a tracking unit which performs tracking of a plurality of regions in the ultrasound images that sequentially follow from one time, a first motion information calculating unit which calculates first motion information of the respective regions, based on the track of the tracking unit, and a second motion information calculating unit which calculates second motion information of the measurement reference parts, based on the first motion information of the respective regions obtained by the first motion information calculating unit, wherein the plurality of regions are parts moved with the measurement reference parts and are regions including parts capable of capturing moving factors that are not able to be captured in the tracking of the measurement reference parts between the one ultrasound image and the other ultrasound image at the tracking by the tracking unit.

In a second aspect, a measuring apparatus is provided. The measuring apparatus is equipped with a measurement reference part setting unit which sets measurement reference parts to parts at which periodic motion is repeated in ultrasound images of a subject, a tracking unit which tracks the measurement reference parts in the ultrasound images that sequentially follow from one time, and a motion information correcting unit which corrects motion information of each of the measurement reference parts, obtained by the tracking by the tracking unit, based on a position of the measurement reference part in the ultrasound image at the one time and a position of the measurement reference part in the ultrasound image different in time from the one time and identical in time phase to the one time.

In a third aspect, a measuring apparatus is provided. The measuring apparatus is equipped with a measurement reference part setting unit which sets measurement reference parts to parts at which periodic motion is repeated in ultrasound images of a subject, a tracking unit which tracks the measurement reference parts in the ultrasound images that sequentially follow from one time, and a motion information correcting unit which defines as a result of correction of a trajectory of the measurement reference parts, a closed curve having the same length as that of the trajectory of the measurement reference parts obtained by tracking by the tracking unit and passing through at least the measurement reference parts in the ultrasound image at the one time.

According to the first aspect, the first motion information is calculated based on the motion information of the plural regions being the parts moved with the measurement reference parts and including the parts capable of capturing the moving factors hard to track in the tracking of each measurement reference part between the one ultrasound image and the other ultrasound image. It is therefore possible to obtain motion information more accurate than conventional with respect to the measurement reference parts.

Further, according to second aspect, the motion information of each of the measurement reference parts, obtained by the tracking by the tracking unit is corrected based on the position of the measurement reference part in the ultrasound image at the one time and the position of the measurement reference part in the ultrasound image different in time from the one time and identical in time phase to the one time. It is therefore possible to obtain motion information more accurate than conventional with respect to the measurement reference parts.

Furthermore, according to the third aspect, the closed curve having the same length as that of the trajectory of the measurement reference parts obtained by tracking by the tracking unit and passing through at least the measurement reference parts in the ultrasound image at the one time is taken as the result of correction of the trajectory of the measurement reference parts. It is therefore possible to obtain motion information more accurate than conventional with respect to the measurement reference parts.

Further advantages will be apparent from the following description of exemplary embodiments illustrated in the accompanying drawings.

DETAILED DESCRIPTION OF THE INVENTION

Exemplary embodiments will hereinafter be described in detail.

First Embodiment

Figure 1:
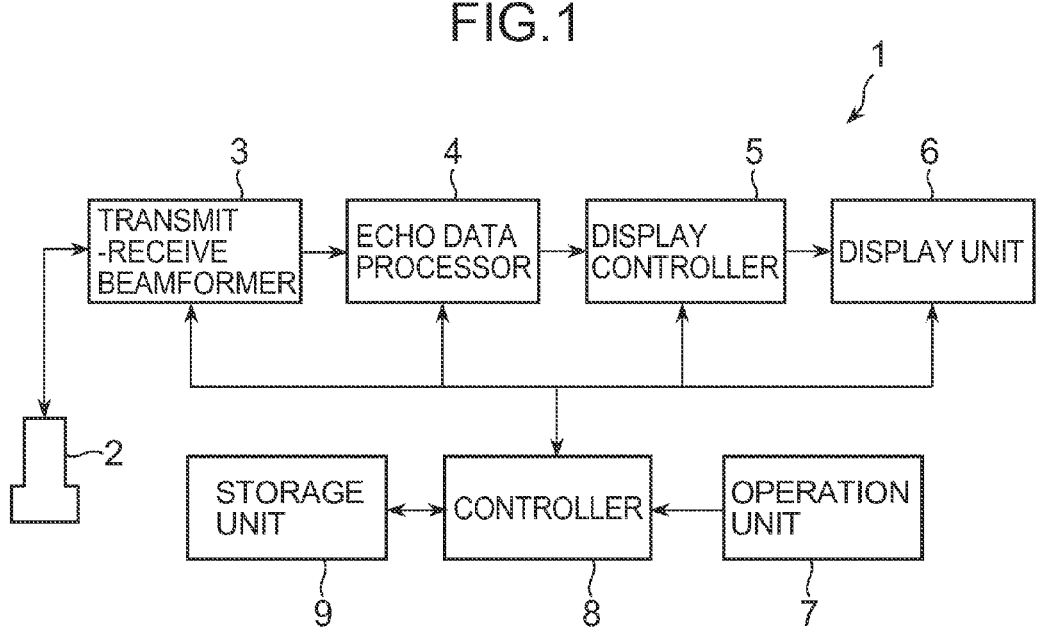
FIG. 1 is a block diagram showing one example of a schematic configuration of an ultrasonic diagnostic apparatus according to a first embodiment.

A first embodiment will first be described based on FIGS. 1 through 12. An ultrasonic diagnostic apparatus 1 shown in FIG. 1 is equipped with an ultrasonic probe 2, a transmit-receive beamformer 3, an echo data processor 4, a display controller 5, a display unit 6, an operation unit 7, a controller 8 and a storage unit 9. The ultrasonic diagnostic apparatus 1 is one example illustrative of an embodiment of a measuring apparatus.

The ultrasonic probe 2 includes a plurality of ultrasonic transducers (not shown) arranged in array form. The ultrasonic probe 2 transmits ultrasound to a subject through the ultrasonic transducers and receives its echo signals therein.

The transmit-receive beamformer 3 supplies an electric signal for transmitting ultrasound from the ultrasonic probe 2 under a predetermined scan condition to the ultrasonic probe 2, based on a control signal outputted from the controller 8. Also, the transmit-receive beamformer 3 performs signal processing such as A/D conversion, phasing-adding processing and the like on each echo signal received by the ultrasonic probe 2 and outputs echo data subsequent to the signal processing to the echo data processor 4.

The echo data processor 4 performs signal processing for generating an ultrasound image on the echo data outputted from the transmit-receive beamformer 3. For example, the echo data processor 4 performs B-mode processing including logarithmic compression processing and envelope detection processing or the like to generate B-mode data.

The display controller 5 performs scan conversion based on a scan converter on the B-mode data to generate B-mode image data. The display controller 5 causes the display unit 6 to display a B-mode image based on the B-mode image data. Also, the display controller 5 causes the display unit 6 to display other indications such as regions of interest or the like to be described later.

The display unit 6 includes an LCD (Liquid Crystal Display), a CRT (Cathode Ray Tube) or the like. The operation unit 7 includes a keyboard and a pointing device or the like for inputting instructions and information by an operator.

The controller 8 is a CPU (Central Processing Unit) and reads a control program stored in the storage unit 9 to execute functions at the respective parts of the ultrasonic diagnostic apparatus 1. For example, the functions of the transmit-receive beamformer 3, the echo data processor 4 and the display controller 5 may be executed by the control program.

Figure 2:
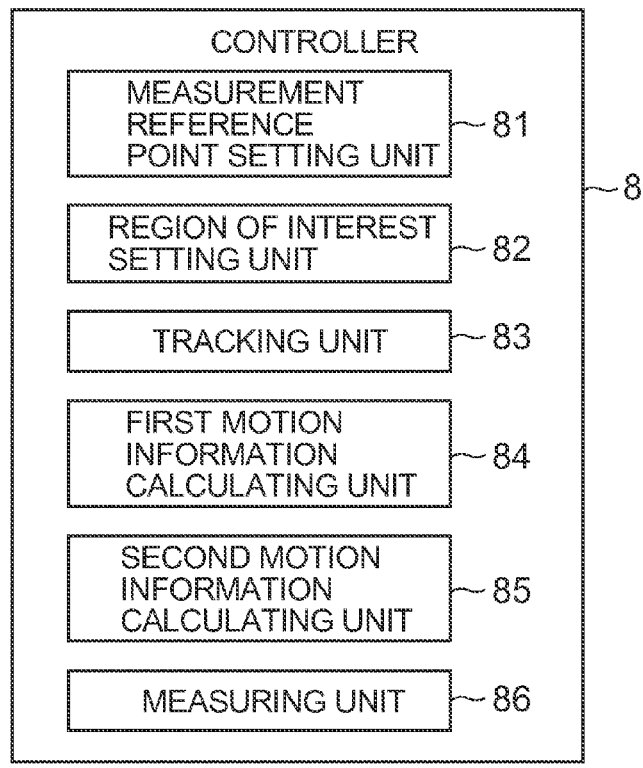
FIG. 2 is a block diagram of functions executed by a controller in the first embodiment.

Further, the controller 8 causes the functions of a measurement reference point setting unit 81, a region of interest setting unit 82, a tracking unit 83, a first motion information calculating unit 84, a second motion information calculating unit 85, and a measuring unit 86 shown in FIG. 2 to be executed. The details thereof will be described later.

The storage unit 9 is, for example, an HDD (Hard Disk Drive), a semiconductor memory or the like.

Figure 3:
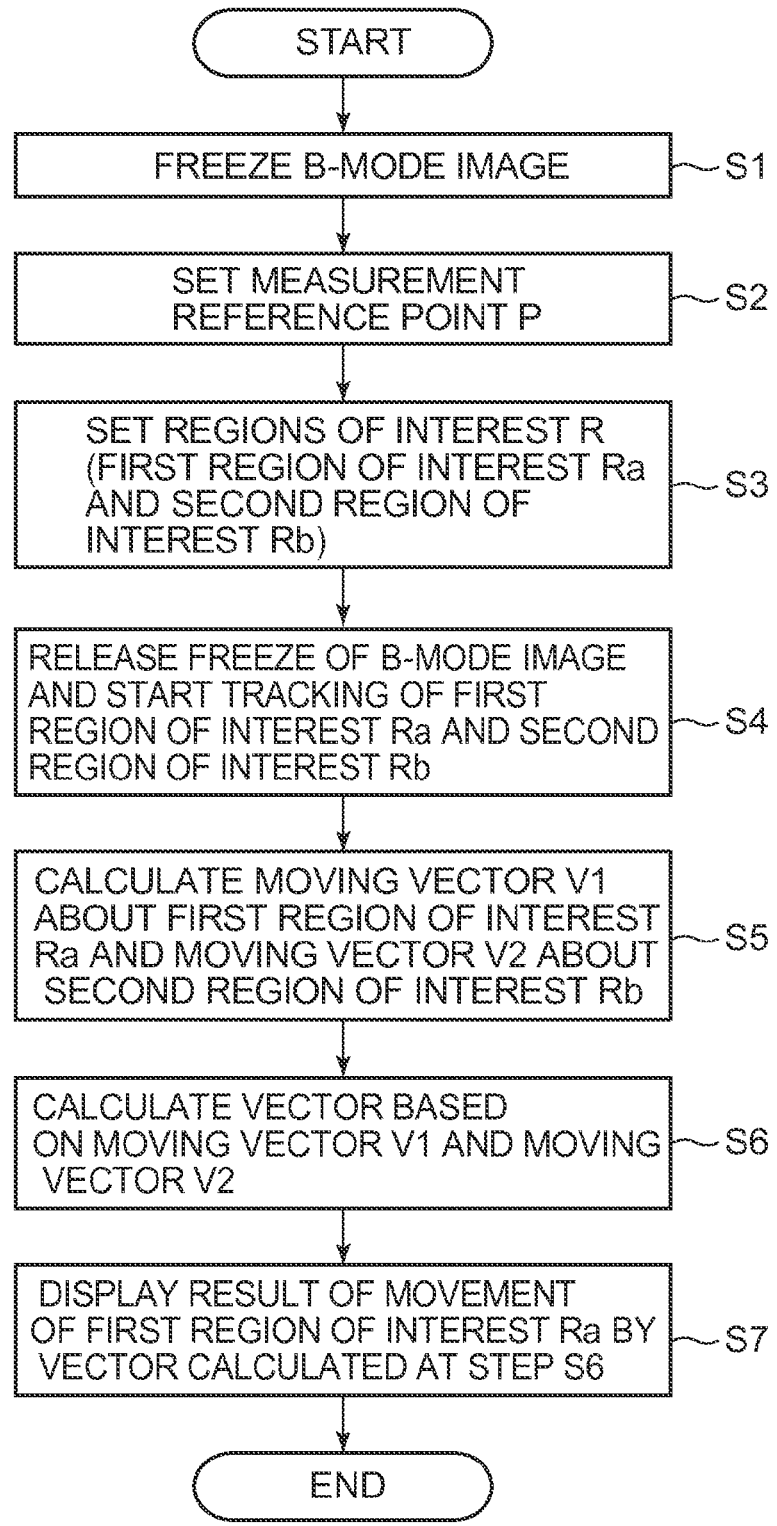
FIG. 3 is a flowchart showing one example of the operation of the ultrasonic diagnostic apparatus according to the first embodiment.

The operation of the ultrasonic diagnostic apparatus 1 according to the first embodiment will be explained based on the flowchart of FIG. 3. First, at Step S1, the operator performs the operation of freezing a B-mode image displayed on the display unit 6 based on the echo signals of ultrasound acquired from the subject.

Figure 4:
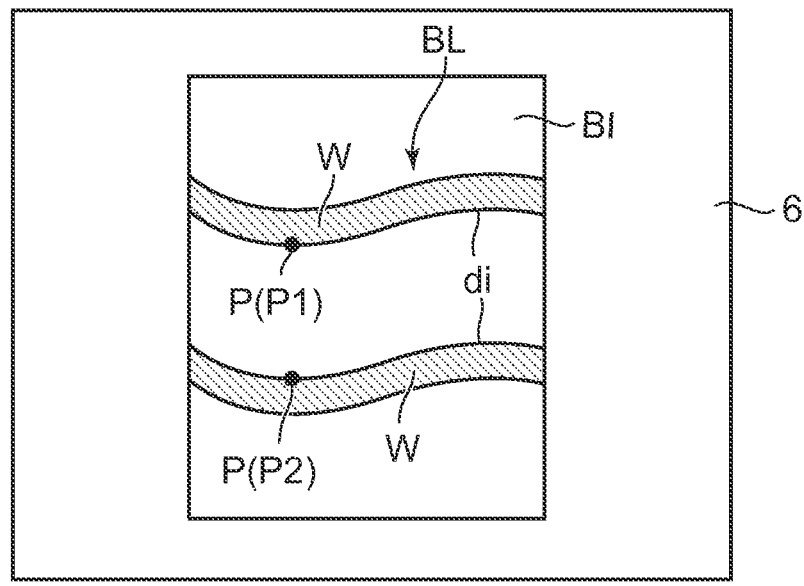
FIG. 4 is a diagram illustrating a display unit on which a B-mode image to which measurement reference points are set is displayed.

Next, at Step S2, the operator sets measurement reference points P as shown in FIG. 4 in the B-mode image BI displayed on the display unit 6. In FIG. 4, two measurement reference points P1 and P2 are set to an inner wall surface of a vascular wall W of a blood vessel BL.

The measurement reference points P are points defined as references for measurement in the B-mode image BI. For example, the measurement reference points P are targets for performing tracking and measuring an amount of movement with respect to a freeze-released B-mode image BI as will be described later. It is also possible to measure a vascular diameter, based on the measurement reference points P.

For example, the operator moves an unillustrated cursor using the pointing device or the like of the operation unit 7 to set the measurement reference points P to desired positions. The measurement reference point setting unit 81 sets the measurement reference points P to the B-mode image BI when there is an input from the operator at the operation unit 7.

As described in Japanese Unexamined Patent Publication No. 2012-90820, after the operator has set one measurement reference point P1 using the pointing device or the like, the support of setting of the measurement reference point P2 may be done in such a manner that a line segment that connects the measurement reference point P1 and the other measurement reference point P2 to each other is orthogonal to the direction of the major axis of a blood vessel.

Figure 5:
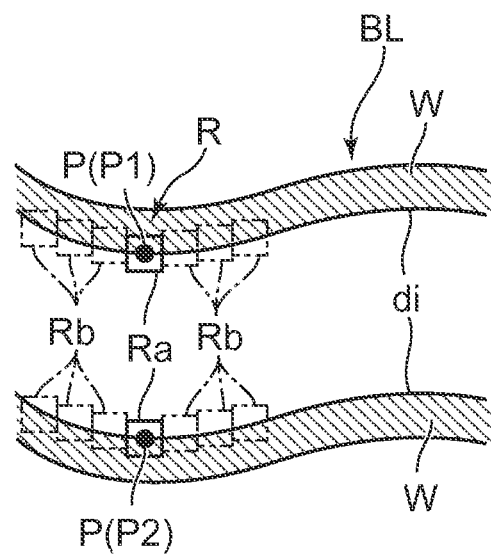
FIG. 5 is a diagram showing a B-mode image of a blood vessel to which regions of interest are set.

Next, at Step S3, the region of interest setting unit 82 sets regions of interest R to the B-mode image BI as shown in FIG. 5. The regions of interest R are first regions of interest Ra each indicated by a solid line and second regions of interest Rb each indicated by a one-dot chain line.

The setting of the regions of interest R will specifically be explained. The region of interest setting unit 82 sets first regions of interest R including the measurement reference points P1 and P2 around the measurement reference points P1 and P2. Also, the region of interest setting unit 82 sets a plurality of second regions of interest Rb to both sides of the first regions of interest Ra along the direction of the major axis of the blood vessel BL. The region of interest setting unit 82 specifies the outline of a vascular wall W, based on a brightness distribution (intensity distribution of echo signals) of a B-mode image BI and sets the second regions of interest Rb so as to include the outline of the vascular wall W. Thus, the second regions of interest Rb are set along the vascular wall W. In the first embodiment, the second regions of interest Rb are set by three on both sides of each of the first regions of interest Ra.

The second regions of interest Rb are parts that move together with the measurement reference points P, which are set including parts capable of capturing moving factors that cannot be captured only by the tracking of the first regions of interest Ra upon the track by the tracking unit 83. This will be described later.

The display controller 5 causes the display unit 6 to display the first regions of interest Ra and the measurement reference points P. On the other hand, the second regions of interest Rb may not be displayed on the display unit 6.

Next, at Step S4, the operator releases the freeze of each B-mode image BI. When its freeze is released, the tracking unit 83 starts the tracking of the first region of interest Ra and the respective second regions of interest Rb at the B-mode images BI that sequentially follow from one time. The tracking of the first region of interest Ra and the second regions of interest Rb is performed, for example, based on the brightness distribution of the B-mode image BI, using a known method such as an optical flow method or the like.

Figure 6:
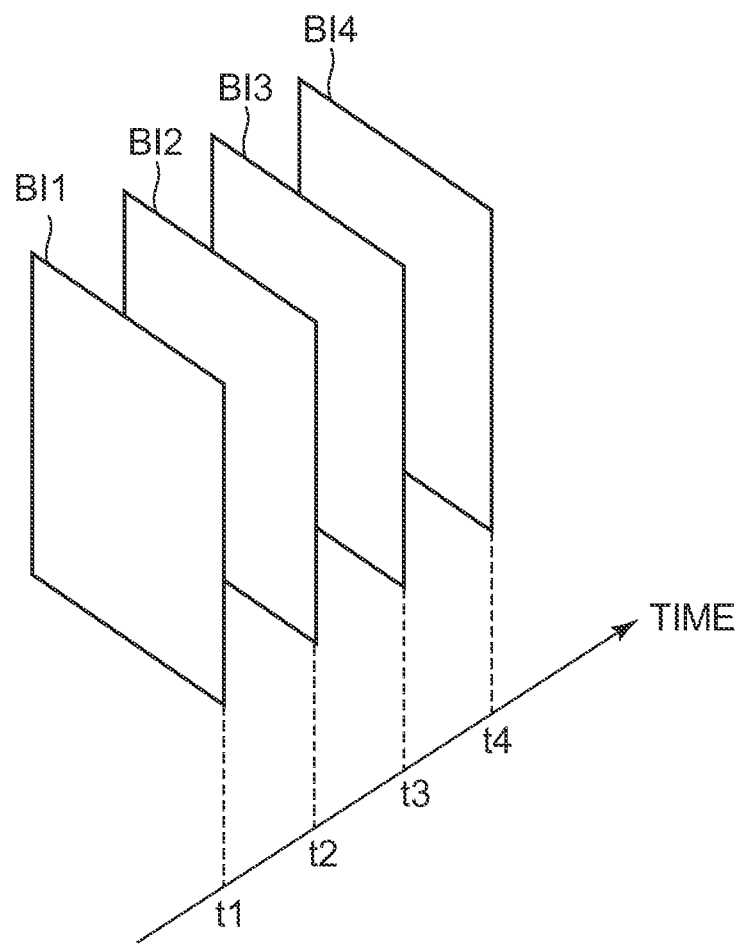
FIG. 6 is a conceptual diagram illustrating B-mode images at times t1, t2, t3 and t4.

Next, at Step S5, the first motion information calculating unit 84 determines a moving vector V1 indicative of movement of a part to which the first region of interest Ra is set in the B-mode image BI, and a moving vector V2 indicative of movement of a part to which the second region of interest Rb is set, based on the track by the tracking unit 83. The first motion information calculating unit 84 determines the movements of the part to which the first region of interest Ra is set and the part to which each of the second region of interests Rb is set, from the track by the tracking unit 83 between two B-mode images BI different in time to thereby calculate the moving vector V1 and the moving vector V2. Assuming that as shown in FIG. 6, for example, B-mode images at times t1, t2, t3, t4, . . . are respectively B-mode images BI1, BI2, BI3, BI4, . . . , the calculation of the moving vectors V1 and V2 is done between the B-mode images BI1 and BI2, between the B-mode images BI2 and BI3 and between the B-mode images BI3 and BI4.

Next, at Step S6, the second motion information calculating unit 85 calculates a vector on which the moving vector V1 and a plurality of the moving vectors V2 are reflected. In the first embodiment, the second motion information calculating unit 85 calculates an average vector Vav of the moving vector V1 and a plurality of the moving vector V2 as the vector. The second motion information calculating unit 85 may calculate the average vector Vav except for the vectors extremely different in magnitude and direction, of the moving vectors V1 and V2. Also, the second motion information calculating unit 85 may multiply the moving vectors V1 and V2 by weighting factors each corresponding to the magnitude of a correlation coefficient obtained in the optical flow method used in the tracking for obtaining their vectors and thereby calculate the average vector Vav.

Next, at Step S7, the display controller 5 causes the display unit 6 to display a result of movement (result of movement of the measurement reference point P) of each of the first regions of interest Ra by the average vector Vav. Thus, as a measurement result of the amount of movement of each measurement reference point P, motion information based on the average vector Vav is displayed and corrected motion information (post-correction motion information) about the measurement reference point P is displayed.

Figure 7:
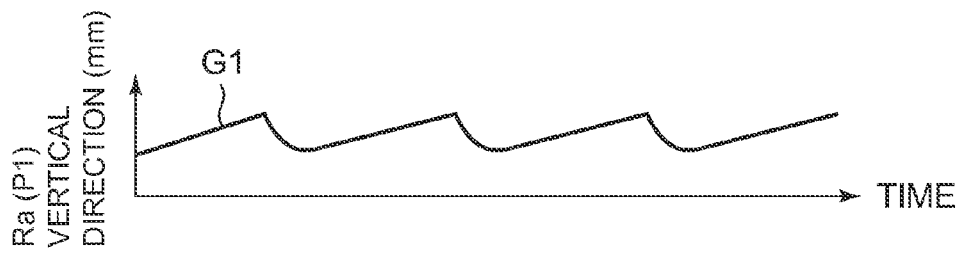
FIG. 7 is a diagram depicting a graph of a result of movement of a first region of interest Ra about a measurement reference point P1 in the vertical direction.
Figure 8:
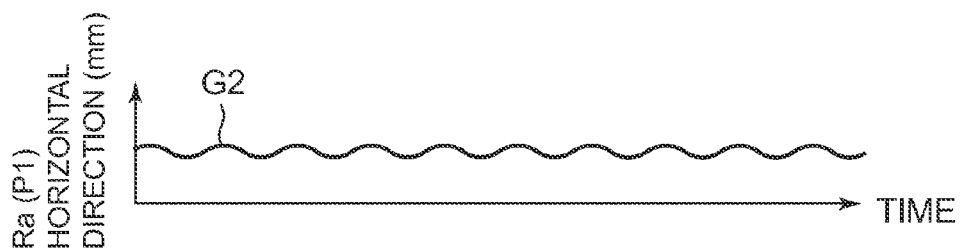
FIG. 8 is a diagram showing a graph of a result of movement of the first region of interest Ra about the measurement reference point P1 in the horizontal direction.
Figure 9:
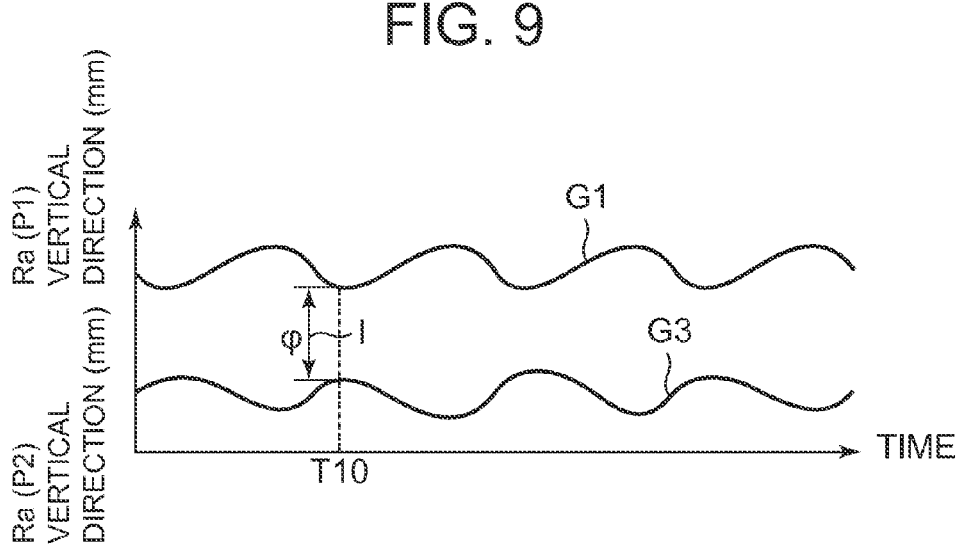
FIG. 9 is a diagram showing a graph of a result of movement of the first region of interest Ra about the measurement reference point P1 in the vertical direction and a graph of a result of movement of a first region of interest Ra about a measurement reference point P2 in the vertical direction.

For example, as shown in FIG. 7, the display controller 5 may display a graph G1 indicative of a result of movement of the first region of interest Ra about the measurement reference point P1 in the vertical direction by the average vector Vav. Also, as shown in FIG. 8, the display controller 5 may display a graph G2 indicative of a result of movement of the first region of interest Ra about the measurement reference point P1 in the horizontal direction by the average vector Vav. Further, as shown in FIG. 9, the display controller 5 may display on a coordinate plane comprised of the same coordinate axis, a graph G1 indicative of a result of movement of the first region of interest Ra about the measurement reference point P1 in the vertical direction by the average vector Vav, and a graph G3 indicative of a result of movement of the first region of interest Ra about the measurement reference point P2 in the vertical direction by the average vector Vav.

Incidentally, the average vector Vav is post-correction motion information between two B-mode images. One point on each of the graphs G1 through G3 is obtained from the average vector Vav defined as one. Thus, an average vector Vav1 obtained from the B-mode images BI1 and BI2 at the times t1 and t2, an average vector Vav2 obtained from the B-mode images BI2 and BI3 at the times t2 and t3, an average vector Vav3 obtained from the B-mode images BI3 and BI4 at the times t3 and t4, . . . are sequentially calculated so that the graphs G1 through G3 are displayed.

Here, the vertical direction means the vertical direction (depth direction) in the B-mode image BI. The horizontal direction means the direction orthogonal to the vertical direction in the B-mode image BI.

The graphs G1 through G3 will be explained. The horizontal axes of the graphs G1 through G3 respectively indicate the time. The vertical axes of the graphs G1 and G3 respectively indicate the vertical positions in the B-mode image BI, of the first regions of interest Ra about the measurement reference points P1 and P2. The vertical axis of the graph G2 indicates the horizontal position in the B-mode image BI, of the first region of interest Ra about the measurement reference point P1.

In the graphs G1 and G3 shown in FIG. 9, the difference in the vertical direction therebetween at the same time means the inner diameter φ of a blood vessel BL. Thus, the operator causes the display unit 6 (not shown in FIG. 9) to display an inner diameter index I using the operation unit 7 and matches both ends of the inner diameter index I with the graphs G1 and G3. Thus, the measuring unit 86 measures the inner diameter φ. In FIG. 9, the inner diameter φ is measured at a time T10.

Figure 10:
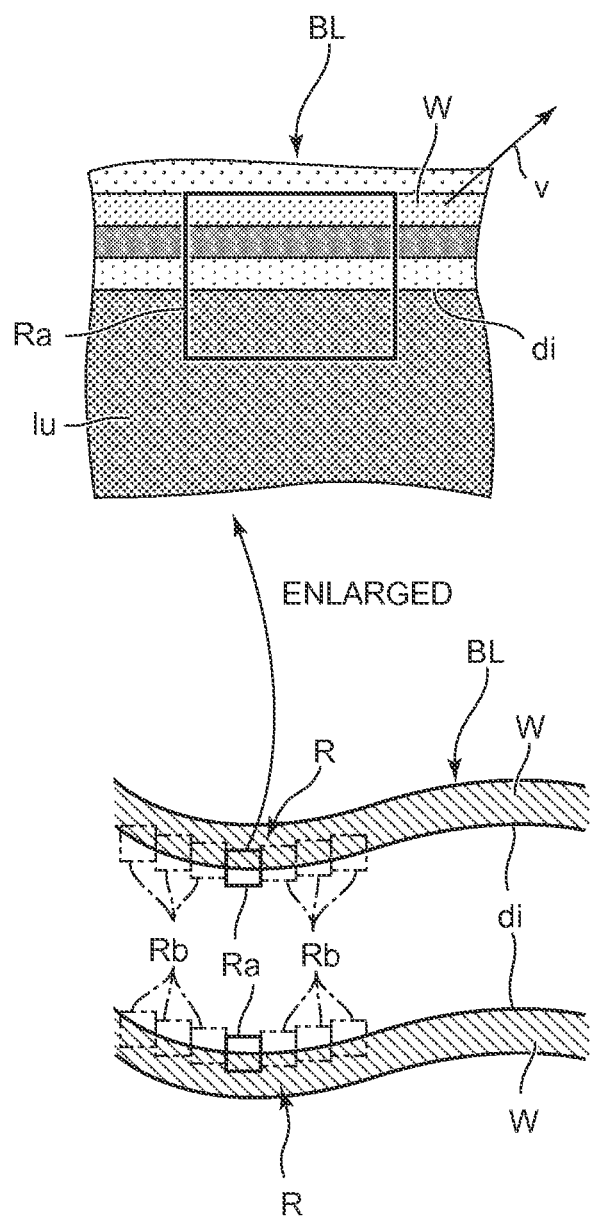
FIG. 10 is a diagram for describing the reason why a vector calculated at Step S6 is used as a result of movement of the first region of interest.

A description will now be made of the reason why the vector (the average vector Vav in the first embodiment) based on the moving vector V1 and a plurality of the moving vectors V2 is used as the result of movement of the first region of interest Ra. An enlarged diagram of the vicinity of the first region of interest Ra is shown above FIG. 10. As shown in the enlarged diagram, in a B-mode image, a vascular wall W takes a structure in which parts similar in brightness are arranged in a laminated form in the major-axis direction of a blood vessel BL (direction in which the vascular wall W extends). In FIG. 10, an inner wall surface di of the vascular wall W and a layer of the vascular wall W are linearly shown in a simplified form. Incidentally, in the B-mode image, a lumen part lu of the blood vessel BL looks like having fallen out black.

Figure 11:
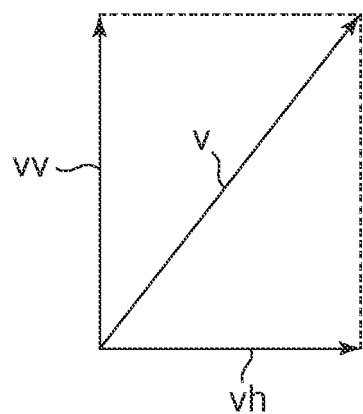
FIG. 11 is an exploded diagram of the vector shown in FIG. 10.

The first region of interest Ra is set to each horizontally-extending part of the vascular wall W. Assume that when the first region of interest Ra is set to such a position, the blood vessel BL is moved in an oblique direction indicated by a vector v. Factors for this movement include, as shown in FIG. 11, for example, a vector vv being a factor for movement in a vertical direction by pulsation, and a vector vh being a factor for movement in a horizontal direction by an inertial force with the movement of blood within the blood vessel BL.

Figure 12:
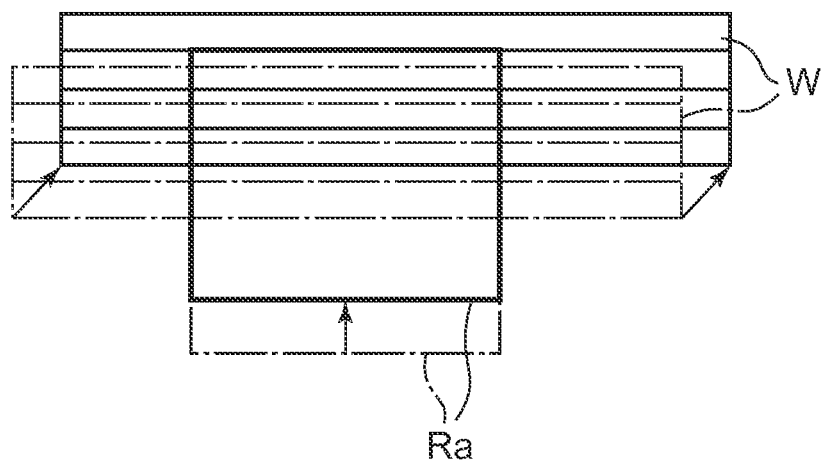
FIG. 12 is a diagram for describing the movement of a vascular wall and the tracking of a first region of interest.

Since, however, the brightness distribution of the B-mode image remains almost unchanged in the horizontal direction, the movement in the vertical direction can be captured when the first region of interest Ra is tracked based on the brightness distribution, but the movement in the horizontal direction becomes difficult to be captured. Thus, as shown in FIG. 12, in spite of the vascular wall W being moved in the oblique direction, the result of tracking of the first region of interest Ra by the tracking unit 83 leads to its movement only in the vertical direction.

On the other hand, since the part to which each of the second regions of interest Rb is set is a part at which the vascular wall W extends in the oblique direction, a change in brightness occurs even in the horizontal direction. Thus, the result of tracking of the second region of interest Rb by the tracking unit 83 leads to a track result including even moving factors in the horizontal direction, which cannot be captured in the case of the tracking of the first region of interest Ra. Since the average vector Vav on which such a moving vector V2 of second region of interest Rb is also reflected is defined as the result of movement of the first region of interest Ra, motion information more accurate than conventional can be obtained with respect to each measurement reference point P.

Next, modifications of the first embodiment will be explained. In the first modification, at Step S6 described above, each of the vectors calculated based on the moving vector V1 and a plurality of the moving vectors V2 may be an intermediate vector of the moving vector V1 and the plurality of moving vectors V2. The intermediate vector means, for example, a vector having a magnitude equivalent to half of a composite vector obtained by combining the minimum vector and the maximum vector of the moving vector V1 and the plural moving vectors V2.

Figure 13:
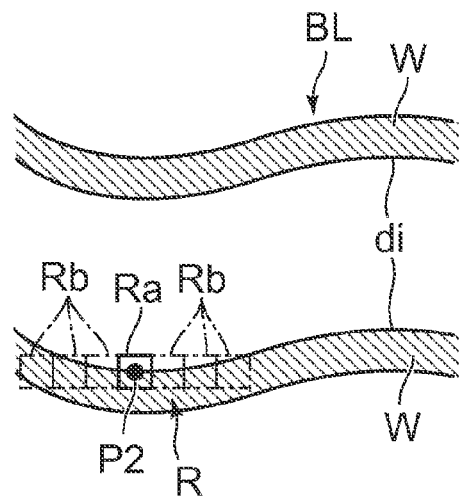
FIG. 13 is a diagram showing an example of setting of second regions of interest in a second modification of the first embodiment.
Figure 14:
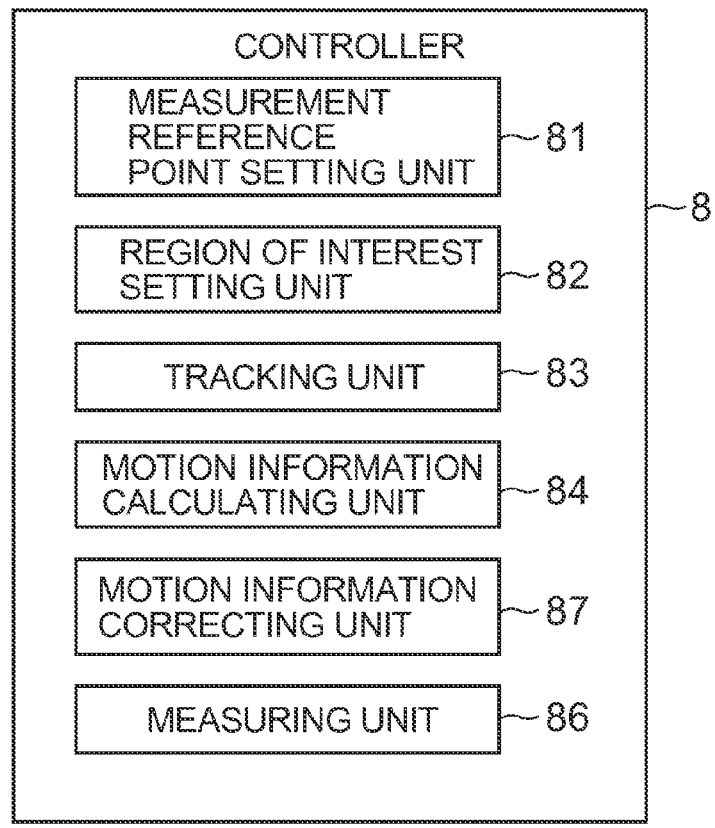
FIG. 14 is a block diagram of functions executed by a controller in a second embodiment.

The second modification will next be described. In the second modification, as shown in FIG. 13, the second regions of interest Rb may be linearly set to both sides of the first region of interest Ra without being set along the outline of the vascular wall W. The second regions of interest Rb set to both side of the first region of interest Ra about the measurement reference point P2 are shown in FIG. 13.

Second Embodiment

A second embodiment will next be described. In the second embodiment, the controller 8 causes the functions of a measurement reference point setting unit 81, a region of interest setting unit 82, a tracking unit 83, a first motion information calculating unit 84, a motion information correcting unit 87 and a measuring unit 86 to be executed. The controller 8 in the second embodiment is different from that in the first embodiment, and includes the motion information correcting unit 87 but does not include the second motion information calculating unit 85.

Figure 15:
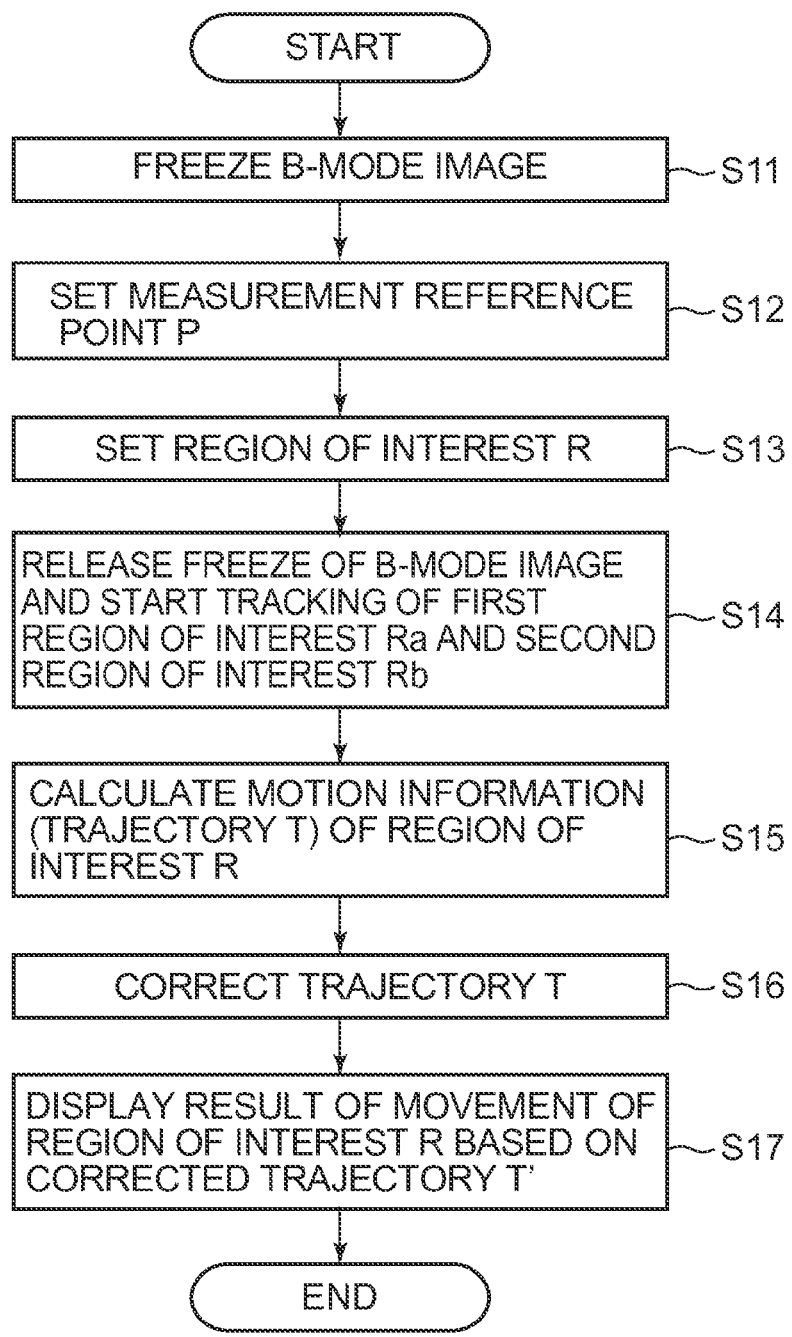
FIG. 15 is a flowchart showing one example of the operation of an ultrasonic diagnostic apparatus according to the second embodiment.

The operation of the ultrasonic diagnostic apparatus 1 according to the second embodiment will next be described based on the flowchart of FIG. 15. Step S11 of FIG. 15 is the same process as at Step S1 of FIG. 3, and Step S12 of FIG. 15 is the same process as at Step S2 of FIG. 3. Their description will therefore be omitted.

Figure 16:
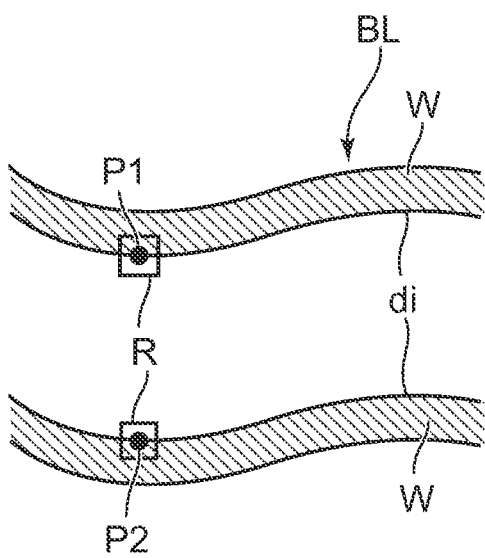
FIG. 16 is a diagram illustrating a B-mode image of a blood vessel to which regions of interest are set in the second embodiment.

Next, at Step S13, as shown in FIG. 16, regions of interest R including measurement reference points P1 and P2 set at Step S12 described above are set around the measurement reference points P1 and P2. The regions of interest R are the same as the first regions of interest Ra in the first embodiment.

Next, at Step S14, the operator releases the freeze of a B-mode image in a manner similar to Step S4 described above. When released, the tracking unit 83 starts the tracking of the regions of interest R in the B-mode images BI that sequentially follow from one time.

Figure 17:
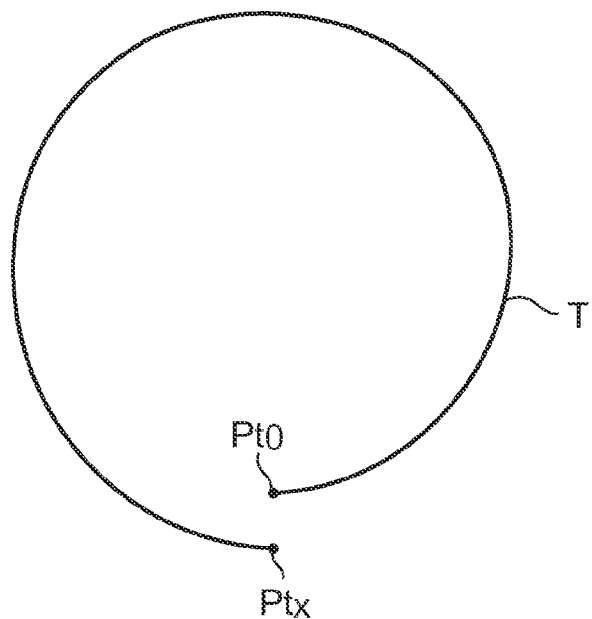
FIG. 17 is a diagram showing one example of a trajectory of movement of regions of interest.

Next, at Step S15, the first motion information calculating unit 84 determines motion information (motion information of the measurement reference points P) of the regions of interest R, based on the track by the tracking unit 83. The motion information is taken as a trajectory T in which the respective regions of interest R are moved as shown in FIG. 17. The trajectory T is formed by connecting points Pt indicative of the positions of the respective regions of interest R at B-mode images BI different in time during one heartbeat to one another as needed. In FIG. 17, however, only two points Pto and PtX (where X is a natural number) at the ends of the trajectory T are shown as the points Pt. Points Pt1, Pt2, . . . , Pt(X−1) therebetween are not shown. The number of points on the trajectory T is (X+1) ranging from the points Pto to PtX.

The trajectory T shown in FIG. 17 is a trajectory of movement of the regions of interest R during one heartbeat. The point Pto is a track starting point (starting point of trajectory T). One heartbeat ranges from the points Pto to PtX. The points Pto and PtX are the positions of the regions of interest R in a state in which a pulsant blood vessel become the maximum diameter or the minimum diameter.

The point Pto corresponds to the position of a measurement reference part in an ultrasound image at one time. The point PtX corresponds to the position of a measurement reference part in each ultrasound image different in time from one time and identical in time phase to the one time.

Here, the vascular wall to which the regions of interest R are set, repeats periodic motion due to its pulsation. Accordingly, the parts to which the regions of interest R are set move with the pulsation and return to their original positions after one heartbeat. Thus, as when the blood vessel is in the state of the maximum diameter or the minimum diameter, the parts to which the regions of interest R are set in the subject are placed in the same positions at the same time phase at the heartbeat.

When, however, the accurate tracking is not done during the tracking of the regions of interest R by the tracking unit 83 as in the case of the moving factors in the horizontal direction being not captured, and the like, the positions of the points Pto and PtX to be placed in the same time phase and the same position are shifted as shown in FIG. 17. Thus, when the trajectory T is obtained as the motion information of the regions of interest R at Step S15 described above, the motion information correcting unit 87 corrects the trajectory T at Step S16 in such a manner that the points Pto and PtX coincide in position with each other.

Figure 18:
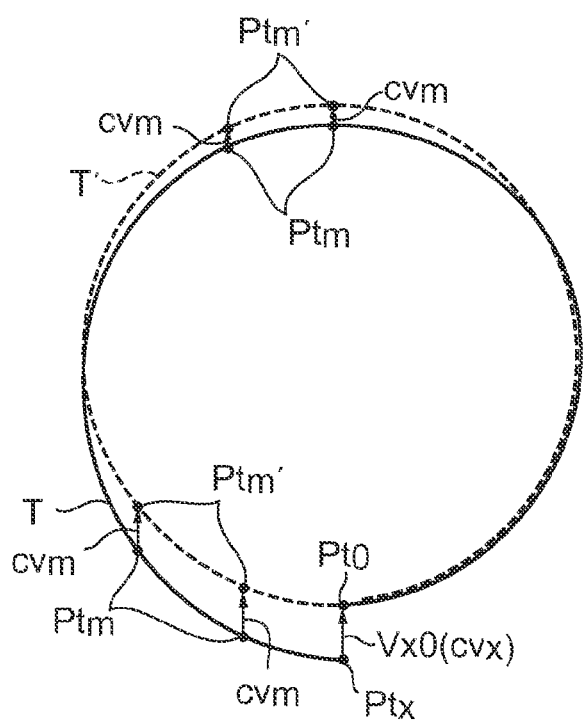
FIG. 18 is a diagram for describing a correction for the trajectory of movement of the regions of interest.

The correction of the trajectory T will be described in detail. The motion information correcting unit 87 determines a vector Vx0 with the point PtX as a starting point and the point Pto as an end point as shown in FIG. 18. Next, the magnitude of a correction vector cvm represented by the following Equation 1 is determined with respect to each point Ptm other than the point Pto (where m is a natural number ranging from 1 to X).

$$cvm = Vx0 \times m / \{(X+1)-1\}$$   Equation 1

In Equation 1, "cvm" is the magnitude of the correction vector, and "Vx0" is the magnitude of the vector Vx0.

The magnitude of the correction vector cvm obtained from Equation 1 is a minimum at the point Pt1 (not shown) and a maximum at the point PtX.

The motion information correcting unit 87 position-corrects the points Ptm (where m: 1, 2, 3, . . . , X) other than the point Pto at the trajectory T by correction vectors cvm each having the magnitude obtained in Equation 1 and the same direction and orientation as the vector Vx0.

Some of the correction vectors cvm (correction vectors cv1 through cvX) are shown in FIG. 18. Points Ptm' where the points Ptm are respectively position-corrected by the correction vectors cvm are obtained. Thus, a corrected trajectory T' (broken line in FIG. 18) is obtained which is formed by connecting the points Ptm' to each other as needed.

Incidentally, the correction vector cvX at the point PtX is the vector Vx0.

When the corrected trajectory T' is obtained at Step S16, the display controller 5 causes the display unit 6 to display the result of movement of the regions of interest R based on the corrected trajectory T' at Step S17. As the result of movement of the regions of interest R based on the corrected trajectory T', a graph G1 (refer to FIG. 7) indicative of the result of movement of the region of interest R about the measurement reference point P1 in the vertical direction, and a graph G2 (refer to FIG. 8) indicative of the result of movement of the region of interest R about the measurement reference point P1 in the horizontal direction may be displayed. Further, a graph G1 indicative of the result of movement of the region of interest R about the measurement reference point P1 in the vertical direction, and a graph G3 indicative of the result of movement of the region of interest R about the measurement reference point P2 in the vertical direction may be displayed on a coordinate plane including the same coordinate axis (refer to FIG. 9).

According to the second embodiment, the result of movement of the regions of interest R based on the corrected trajectory T' is displayed. Therefore, even when the result of tracking by the tracking unit 83 becomes inaccurate due to the presence of the moving factors that cannot be captured by the tracking of the tracking unit 83, and the like, a more accurate result of movement can be displayed.

Figure 19:
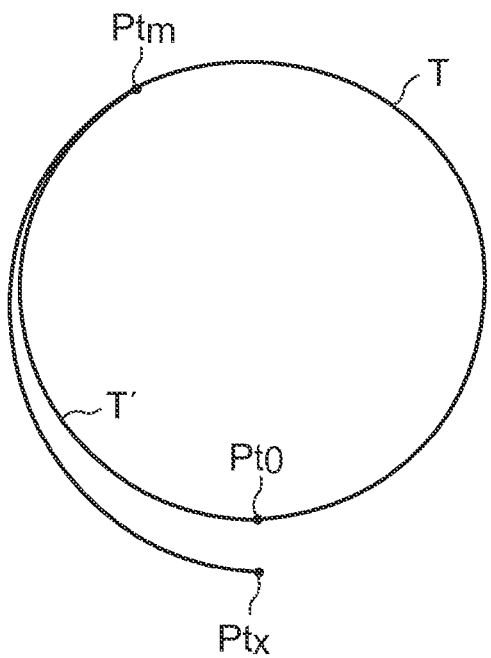
FIG. 19 is a diagram for describing a correction for a trajectory of movement of regions of interest in a modification of the second embodiment.

A modification of the second embodiment will next be described. At Step S16 described above, as shown in FIG. 19, the motion information correcting unit 87 may perform interpolation such as spline interpolation, based on the point, i.e., the point Pto where the point PtX is matched with the point Pto, and an arbitrary point Ptm on the trajectory T and thereby obtain the corrected trajectory T'.

Figure 20:
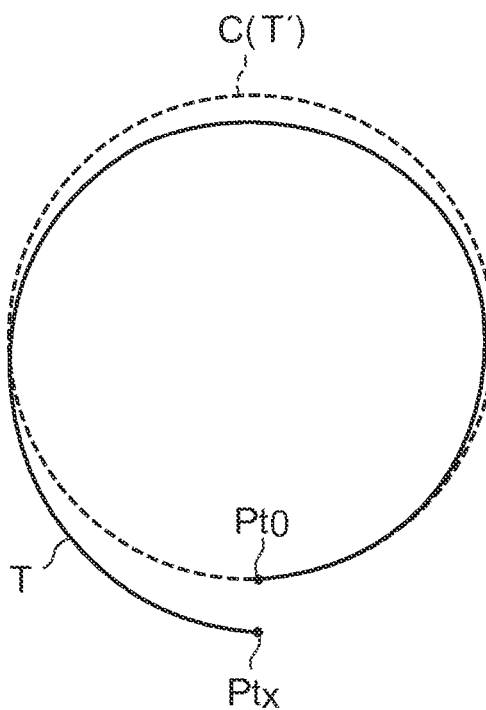
FIG. 20 is a diagram for describing another example of the correction for the trajectory of movement of the regions of interest in the modification of the second embodiment.

Also, at Step S16 described above, the motion information correcting unit 87 may set a circle C having a circumference of the same length as that of the trajectory T and passing through at least the point Pto, as the corrected trajectory T' (broken line in FIG. 20). In this case, the corrected trajectory T' is not necessarily required to be the circle and may be an ellipse, for example. The corrected trajectory T' is a closed curve having the same length as that of the trajectory T and passing through the points Pt in the exemplary embodiment.

Although the disclosure has been described above by exemplary embodiments, it is needless to say that the systems and methods described herein can be changed and implemented in various ways within the scope and the spirit of the invention. For example, the set position of each of the measurement reference points P is not limited to the position described in each of the above exemplary embodiments. For example, although not illustrated in particular, the measurement reference point P may be set to an outer wall surface of a blood vessel.

Many widely different embodiments may be configured without departing from the spirit and the scope of the present invention. It should be understood that the present invention is not limited to the specific embodiments described in the specification, except as defined in the appended claims.

What is claimed is:

1. A measuring apparatus comprising:
a measurement reference point setting unit configured to set a first reference point to each of a plurality of sequential ultrasound images of a subject;
a region of interest setting unit configured to set a first region of interest to a first part including the first reference point, and to set a plurality of second regions of interest to a plurality of second parts in each of the plurality of sequential ultrasound images, where the plurality of second regions of interest are set to both sides of the first region of interest, and where each of the plurality of second regions of interest does not include the first reference point;
a tracking unit configured to perform tracking of the first region of interest and the plurality of second regions of interest in the ultrasound images;
a first motion information calculating unit configured to determine a first moving vector indicative of movement of the first part and a plurality of second moving vectors, where each of the plurality of second moving vectors is indicative of movement of one of the plurality of second regions of interest based on the tracking performed by the tracking unit;
a second motion information calculating unit configured to calculate an average vector based on the first moving vector and the plurality of second moving vectors; and
a display unit configured to display a graph indicative of movement of the first reference point based on the average vector.

2. The measuring apparatus according to claim 1, wherein the plurality of second regions of interest are set along a vascular wall.

3. The measuring apparatus according to claim 1, wherein the region of interest setting unit is further configured to identify a vascular wall in the ultrasound image and set the plurality of second regions of interest to the vascular wall.

4. A measuring method for tracking movement of parts, comprising:
   setting a first reference point to each of a plurality of sequential ultrasound images with a measurement reference point setting unit;
   setting a first region of interest to a first part, the first part including the first reference point;
   setting a plurality of second regions of interest to a plurality of second parts in each of the plurality of sequential ultrasound images, where the plurality of second regions of interest are set to both sides of the first region of interest, where each of the plurality of second regions of interest does not include the first reference point;
   tracking the first region of interest and the plurality of second regions of interest with a tracking unit;
   determining, with a first motion information calculating unit, a first moving vector indicative of movement of the first part based on the tracking;
   determining, with the first motion information calculating unit, a plurality of second moving vectors, where each of the plurality of second moving vectors is indicative of movement of one of the plurality of second regions of interest based on the tracking performed by the tracking unit;
   calculating an average vector based on the first moving vector and the plurality of second moving vectors with a second motion information calculating unit; and
   displaying, on a display unit, a graph indicative of movement of the first reference point based on the average vector.

5. The measuring method of claim 4, wherein setting the plurality of second regions of interest comprises setting the plurality of second regions of interest along a vessel wall.

6. The measuring method of claim 4, wherein the graph represents one of a vertical movement and a horizontal movement of the first reference point.

7. The measuring method of claim 4, further comprising displaying a second graph indicative of movement of the first reference point on the display unit based on the average vector.

8. The method of claim 7, wherein the graph represents one of a vertical movement and a horizontal movement of the first reference point and the second graph represents the other of the vertical movement and the horizontal movement of the first reference point.

9. The method of claim 4, further comprising:
   setting a second reference point to each of the plurality of sequential ultrasound images with the measurement reference point setting unit;
   setting a different first region of interest to a second part including the second reference point, where the second part is different than the first part;
   setting a second plurality of second regions of interest to a second plurality of second parts in each of the plurality of sequential ultrasound images, where the second plurality of second regions of interest are set to both sides of the different first region of interest, where each of the second plurality of second regions of interest does not includes the second reference point;
   tracking the different first region of interest and the second plurality of second regions of interest with the tracking unit;
   determining with the first motion information calculating unit, a different first moving vector indicative of movement of the first part based on the tracking;
   determining with the first motion information calculating unit, a second plurality of second moving vectors, where each of the second plurality of second moving vectors is indicative of movement of one of the second plurality of second regions of interest based on the tracking performed by the tracking unit;
   calculating, with a second motion information calculating unit, a second average vector based on the different first moving vector and the second plurality of second moving vectors;
   displaying, on the display unit at the same time as the graph, a second graph indicative of movement of the second reference point.

10. The method of claim 9, where the first reference point is on a first portion of a vessel and the second reference point is on a second portion of the vessel.

11. The method of claim 10, where the vessel includes a direction of a major axis and a line segment connecting the first reference point to the second reference point is orthogonal to the direction of the major axis.

* * * * *